United States Patent [19]

Wilkie et al.

[11] 4,092,952
[45] June 6, 1978

[54] AUTOMATIC SLIDE STAINER

[76] Inventors: Ronald N. Wilkie; Arman Mooradian, both of 30076 Dequindre, Warren, Mich. 48092

[21] Appl. No.: 826,064

[22] Filed: Aug. 19, 1977

[51] Int. Cl.² .................. B05C 3/04; B05C 3/09; B05C 11/10; B05C 13/00
[52] U.S. Cl. .................. 118/58; 118/425; 118/426; 118/503; 134/80
[58] Field of Search .......... 118/426, 425, 503, 58, 118/64; 134/80, 158

[56] References Cited

U.S. PATENT DOCUMENTS

| 1,130,383 | 3/1915 | Ellison | 118/426 X |
| 2,776,640 | 1/1957 | Miklofsky et al. | 118/426 X |
| 2,908,249 | 10/1959 | Rokosz et al. | 118/425 |
| 3,391,670 | 7/1968 | Lester et al. | 118/426 X |
| 3,853,092 | 12/1974 | Amos et al. | 118/56 |

Primary Examiner—John P. McIntosh
Attorney, Agent, or Firm—Cullen, Settle, Sloman & Cantor

[57] ABSTRACT

An automatic slide stainer has a hollow enclosed framework including a base and a cover, the cover having a top annular platform. A dish is mounted upon said platform for containing a stain solution. A dish of increased width is mounted upon said platform adjacent said first dish and adapted to contain another stain solution. A reservoir tank having an outlet is mounted upon said framework and adapted to contain a rinse solution. A rinse tank is connected to said reservoir and projected up through said platform adjacent said stain dish and has an inlet. A pump is mounted upon said framework having an intake and an outlet. Conduits respectively interconnect the reservoir outlet and pump inlet, and the pump outlet and rinse tank inlet. A power-rotated upright hub is journalled upon said framework centrally of said platform and projects above said cover. A disc-shaped slide retainer plate is mounted upon and centrally secured to said hub for rotation therewith radially inward of said dishes and rinse tank. A series of radially extending slide retainers are pivotally mounted upon said plate around its periphery, each retainer having an outwardly directed clip adapted to supportably receive one end of a slide. Each slide retainer and clip has a raised retained position, a raised dish wall clearance position and a lowered horizontal slide immersion position. Said slide retainers when supporting a slide are normally biased to emersion position. A series of spaced cams are mounted upon said cover inwardly of said platform normally in the path of rotative movement of said slide retainers for momentarily camming the retainers successively to raised dish wall clearance position. Said cams are located adjacent the radial slides of each dish and rinse tank so that said retainers and slides are temporarily cammed to raised clearance position to clear the adjacent walls of said dishes and tank during continuous rotation of said slide retainers.

37 Claims, 14 Drawing Figures

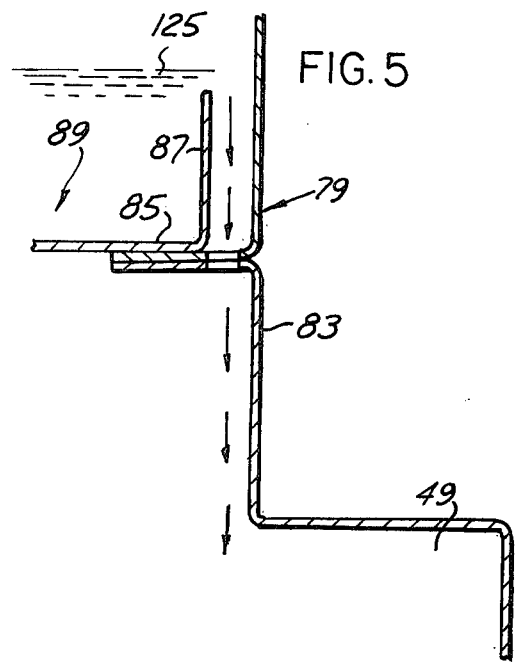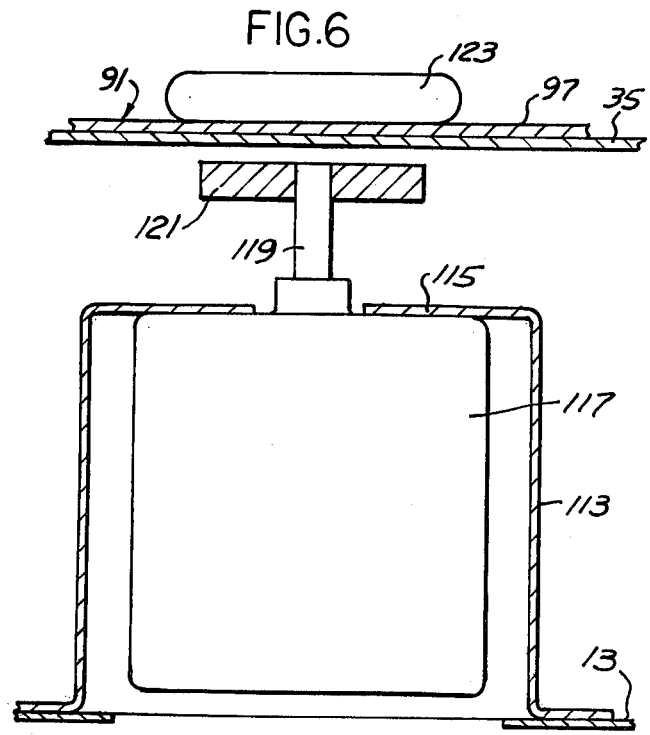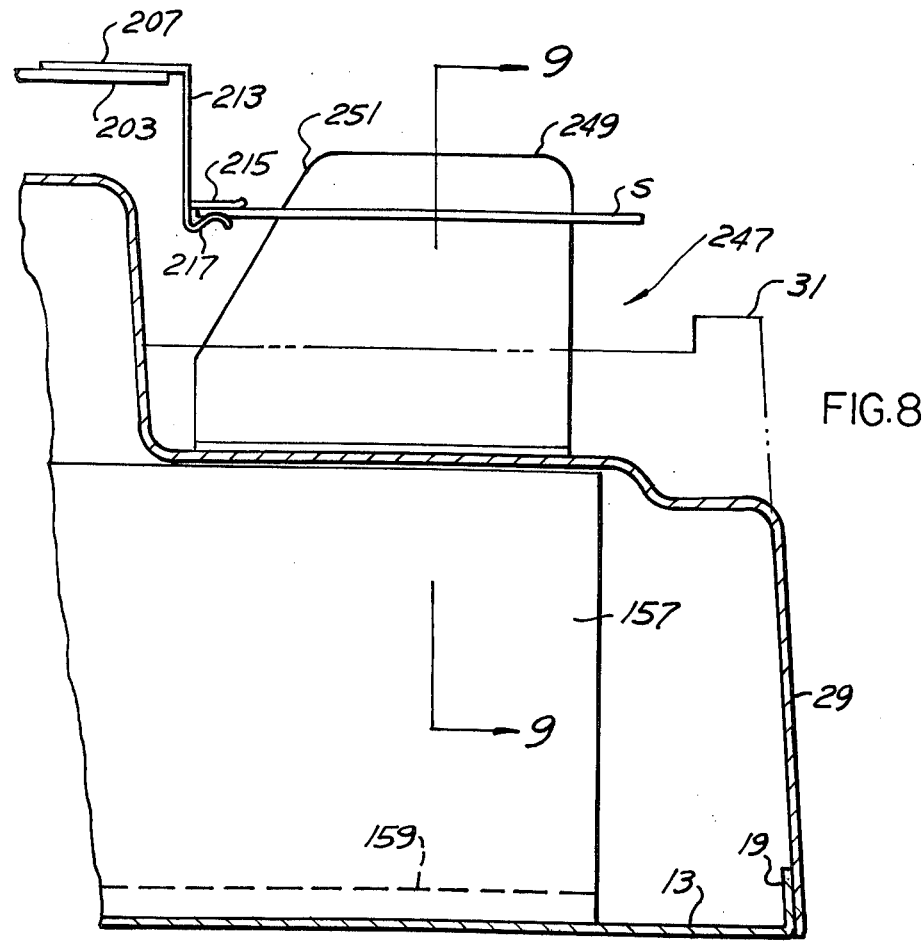

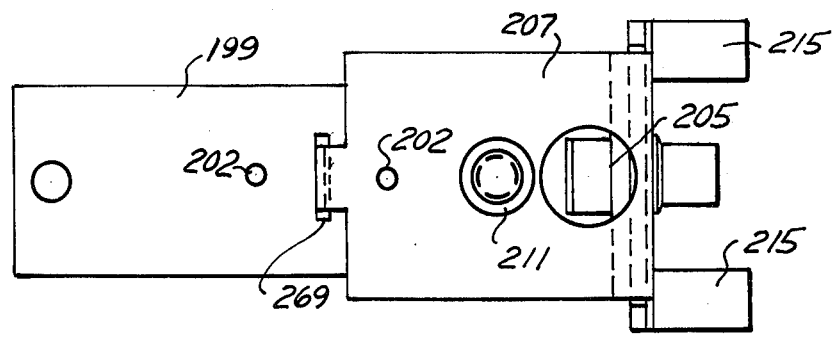
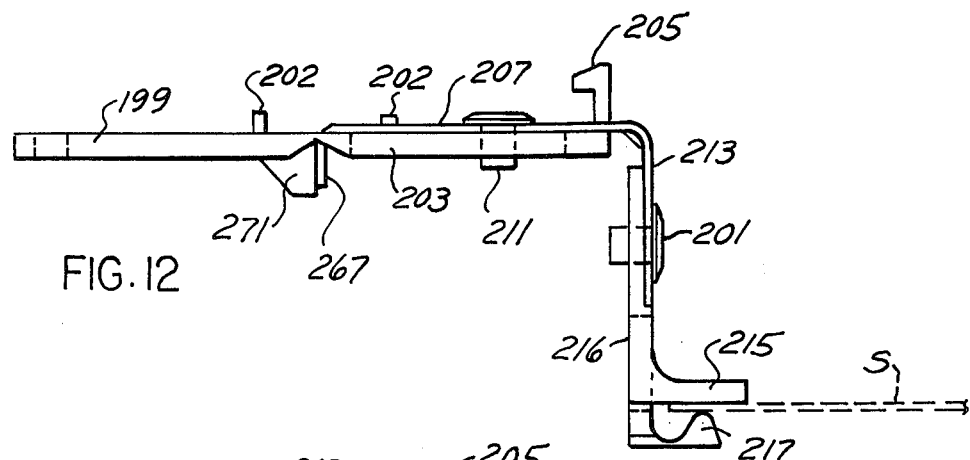
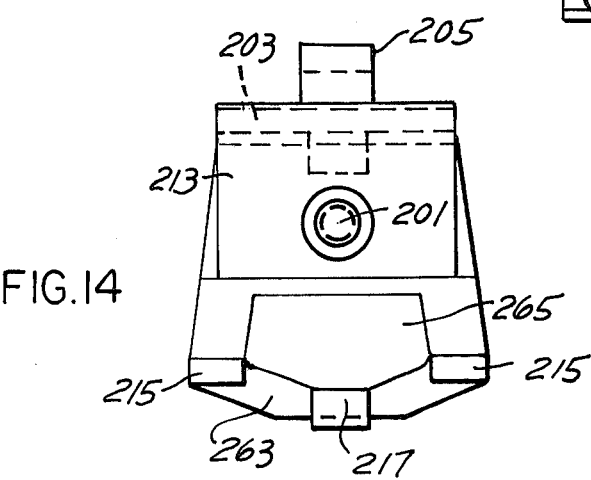

0
AUTOMATIC SLIDE STAINER

BACKGROUND OF THE INVENTION

In preparing blood or tissue specimens for microscopic examination, a small amount of blood or tissue specimen applied to a slide must be first stained. Various efforts have been made to provide mechanical devices for immersing one or a series of such slides in a first stain solution, and successively thereafter into another staining solution and successively thereafter into a rinse tank for the production of stained hemotology or other slides for microscopic examination.

SUMMARY OF THE INVENTION

It is an object of the present invention to provide an improved automatic slide stainer whereby a series of such slides may be mounted upon a slide-staining machine. Throughout a single rotation of each slide, it will be successively emersed within first a solution, a staining solution and a rinse solution and thereafter dried and automatically ejected from the machine in a continuous operation.

It is a further object to provide a slide staining machine which includes a hollow enclosed framework and a cover thereover and mounted upon the top of said cover, a series of dishes containing respectively a first stain solution and an additional staining solution and a rinse tank communicating with a fluid reservoir, together with a pumping device for the continuous circulation of rinsing fluid to and through said rinse tank, together with a power-rotated slide-retainer plate by which, during a single rotation of the slide retainer plate and slides, the respective slides are emersed and passed longitudinally through the respective dishes and tank, successively dried and automatically unloaded all in a continuous operation. Additional solution containing dishes may be employed.

It is a further object to provide an improved slide stainer which includes a rinse water filter and wherein, selectively as desired, the rinse solution before return to the rinse tank may be passed through the filter, and alternately, utilizing a suitable valve, the rinse water may bypass the filter for direct return to the rinsing tank.

It is another object to provide a magnetic stirrer upon the interior of the stain dish adapted for continuous rotation within said tank without mechanical connection to a power-driven rotative source upon the exterior of said dish.

It is a further object to provide a slide-drying hood upon the platform of said stainer and arranged in the path of rotative movement of the respective stained and rinsed slides for drying the slides during continuous movement therethrough.

It is another object to incorporate mechanism for the removal of toxic fumes.

It is another object to provide an automatic slide unloader arranged in the path of rotation of the respective slides to successively strip the slides from their corresponding slide retainer during continuous rotation thereof.

It is a further object to provide an improved lifetime-type of hinge mechanism for the respective slide retainers for hingedly mounting them upon a slide retainer support which is power-rotated, by which the respective slide retainers and associated slides clipped thereto may pivot between a raised retained position, a raised dish wall clearance position and an lowered horizontal emersion position. The stainer includes a series of cams arranged around the stainer cover to automatically cause the slide retainers and associated slides to be moved to an elevated clearance position so as to clear the upright end walls of the respective dishes and rinse tank with said slides automatically dropping by gravity into said tanks into their horizontal position for translation therethrough.

It is a further object to provide an automatic stainer for any type of tissue and including pap smears. The device is applicable to stain Histology or Cytology procedures.

These and other objects will be seen from the following specification and claims in conjunction with the appended drawings.

THE DRAWINGS

FIG. 5 is a fragmentary section taken in the direction of arrows 5—5 of FIG. 1, showing the rinse tank weir with outlet.

FIG. 6 is a fragmentary section taken in the direction of arrows 6—6 of FIG. 1, illustrating the stirring motor assembly.

FIG. 8 is a fragmentary section taken in the direction of arrows 8—8 of FIG. 1, illustrating the slide unloader container.

FIG. 12 is a side elevated view of the hinge slide retainer and spring clips on an enlarged side.

FIG. 13 is a plan view thereof.

FIG. 14 is an end view thereof.

It will be understood that the above drawings illustrate merely a preferred embodiment of the invention and that other embodiments are contemplated within the scope of the Claims hereafter set forth.

DETAILED DESCRIPTION OF THE INVENTION

Figure 1:
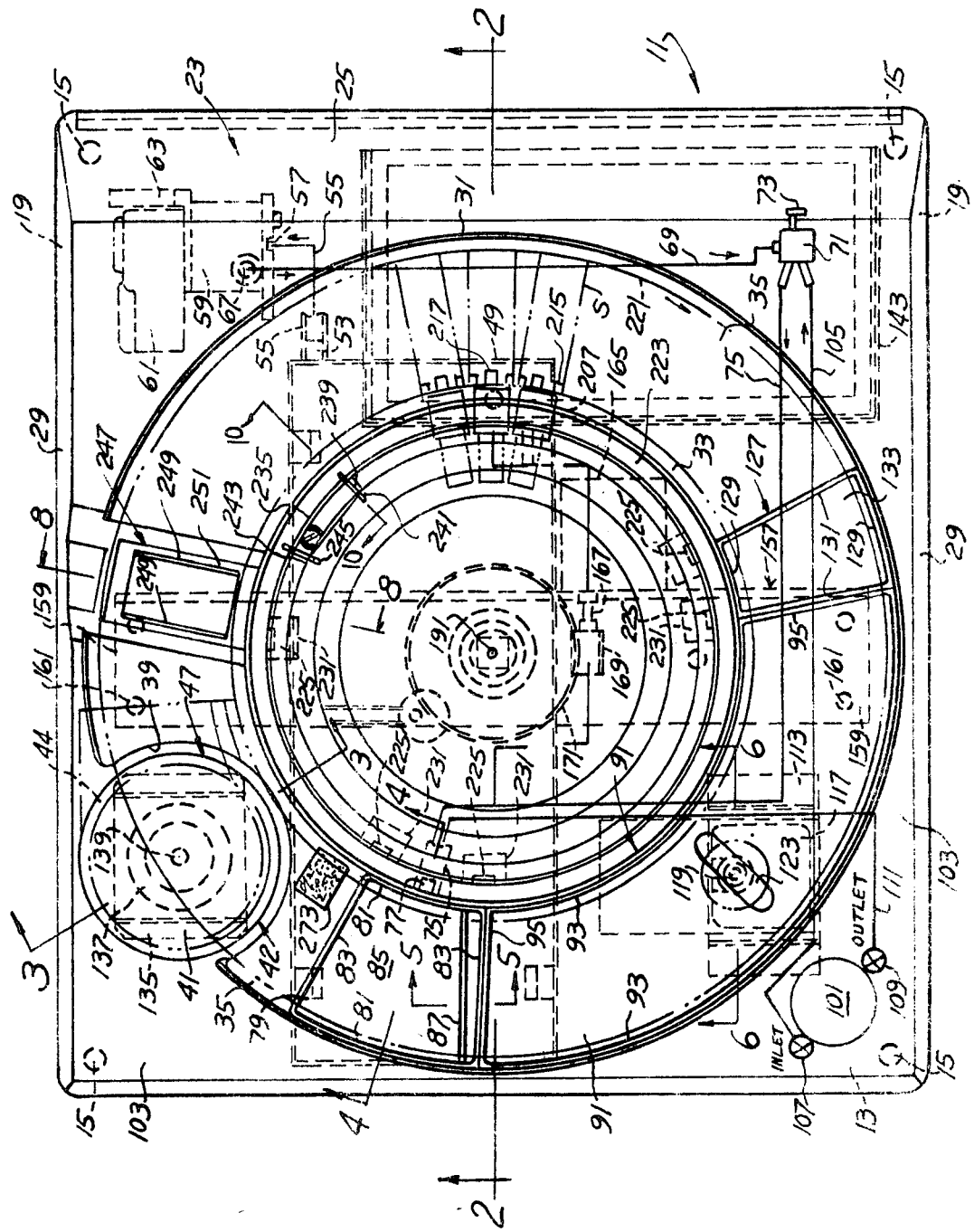
FIG. 1 is a plan view of the present slide stainer.
Figure 2:
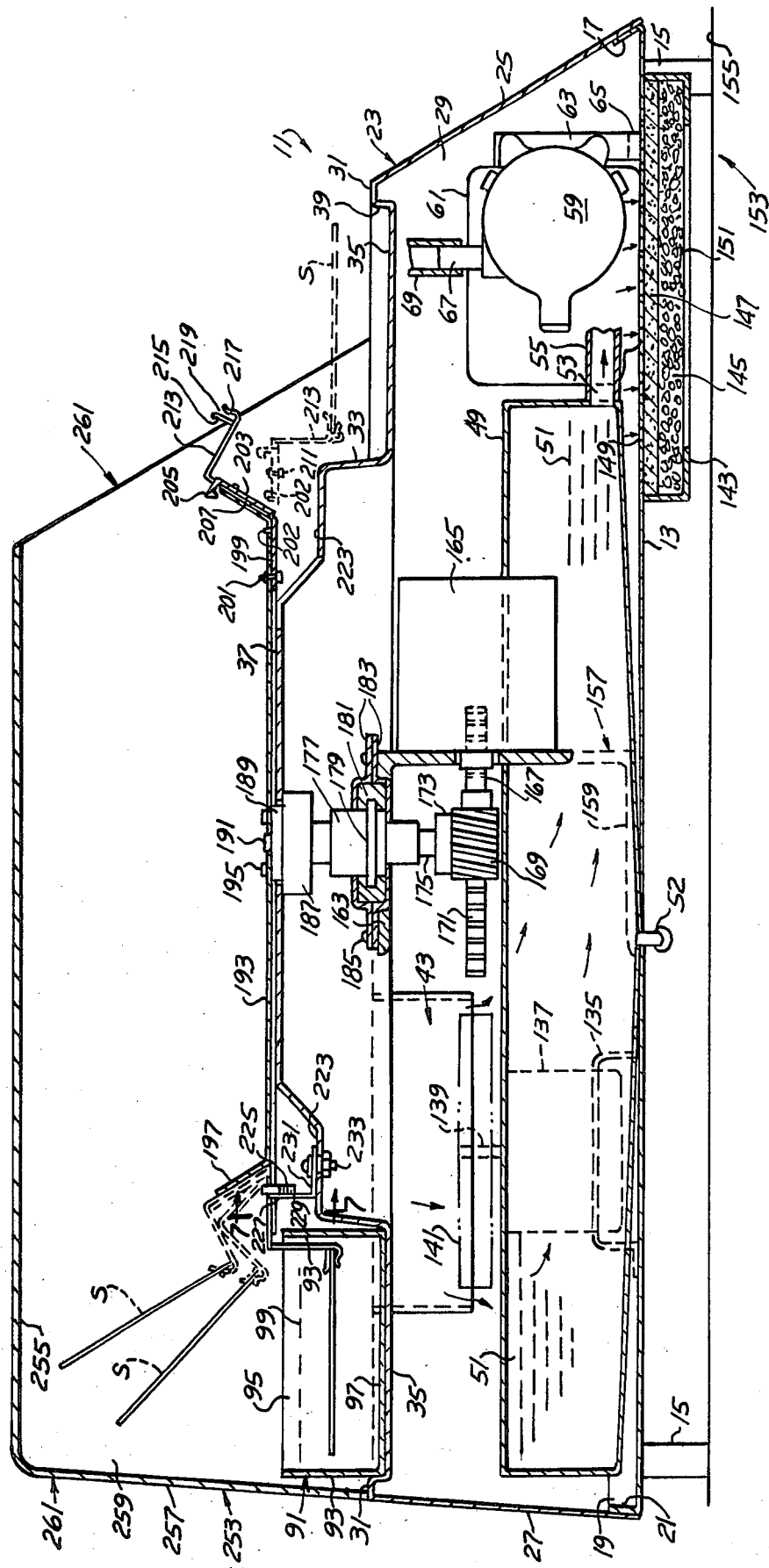
FIG. 2 is a side elevational view thereof partly broken away and sectioned for illustration.

Referring to the drawings and particularly FIGS. 1 and 2, the present slide stainer is generally indicated at 11, includes the horizontally disposed flat base plate 13 with a series of depending corner legs 15. Said base includes the upwardly and rearwardly inclined front flange 17, side flanges 19 and the upright back flange 21.

The slide stainer has a hollow framework which icludes said base plate and a cover 23, preferably of an S.E.O. grade vacuum formed thermoplastic such as P.V.C. acrylic. Said cover includes the upwardly and rearwardly tapered front wall 25, rear wall 27 and side walls 29. These walls at their lower ends are in registry with and suitably secured to the corresponding base flanges 17, 19 and 21, FIG. 2.

The cover includes upon the top thereof a circular ledge or head 31 and radially inward thereof a substantially upright annular wall 33 and therebetween, the annular inset platform 35. Said cover includes inwardly of the annular wall 33 an annular platform 223, and inwardly thereof the circular top 37.

Figure 3:
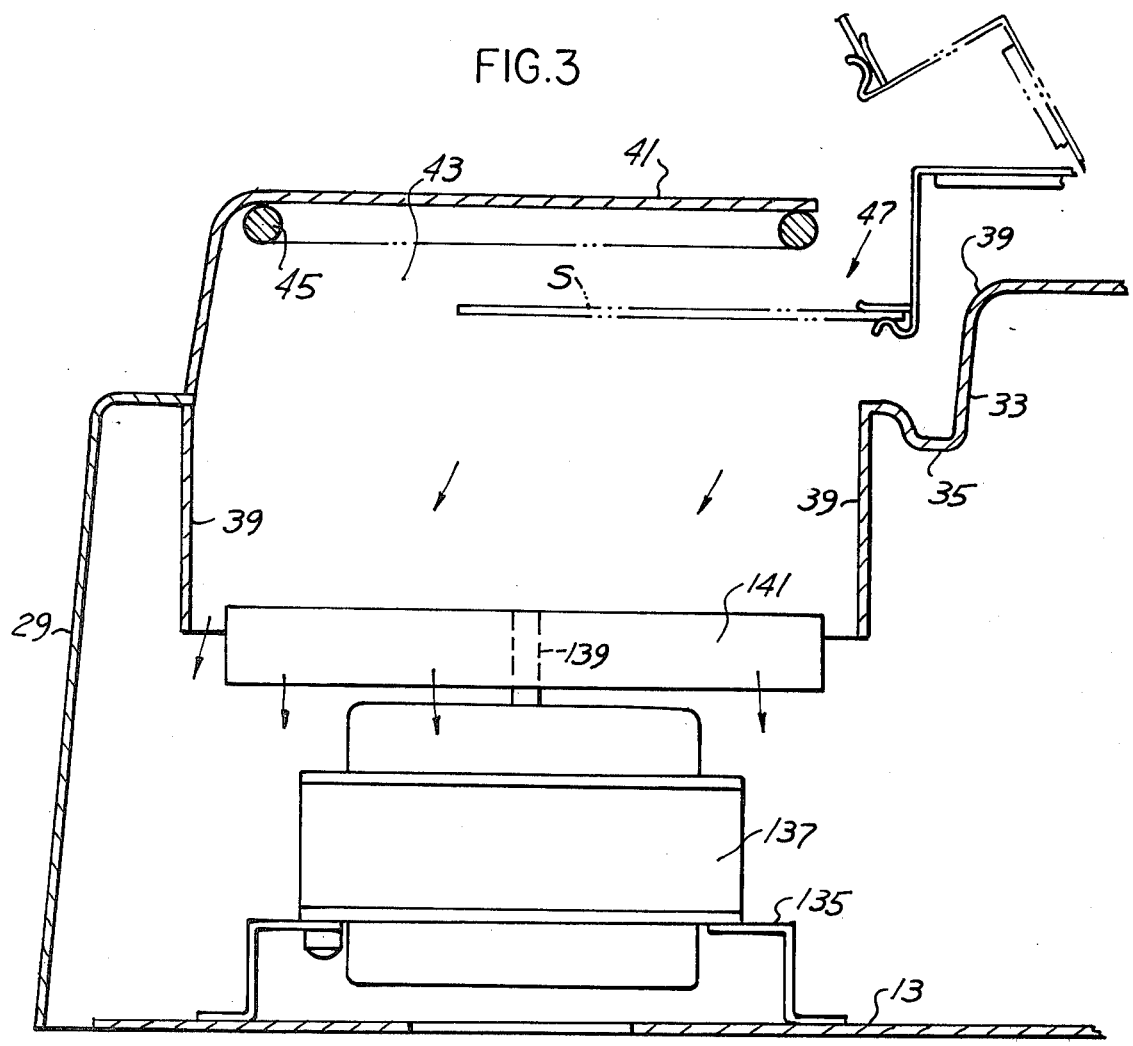
FIG. 3 is a fragmentary section taken in the direction of arrows 3—3 of FIG. 1, illustrating the slide-drying chamber and fume exhauster.

The cover includes an arcuate or circular wall portion 39 adjacent one of the side walls 29 and concentric therewith the circular hood 41, FIGS. 1 and 3. Said hood defines therein the slide-drying chamber 43 and includes upon its undersurface the electric reistance heater 45.

The circular wall 39 in conjunction with said hood, defines therebetween an annular air inlet slot 47 communicating with the drying chamber and utilized further for the exhausting of fumes.

Elongated reservoir tank 49 adapted to contain distilled water 51, or the like, is mounted within said framework upon base 13 and suitably secured thereto and includes on the bottom a drain-fitting 52 which projects through said base. The reservoir tank has an outlet 53, FIGS. 1 and 2, to which is connected one end of the flexible conduit 55. The opposite end of said conduit within the interior of said framework is mounted over the intake 57 of pump 59 whose drive motor 61 is mounted by bracket 63 on base 13 as at 65, FIG. 2.

The pump outlet 67 has connected thereto one end of conduit 69, which extends through the framework with its other end connected to an inlet of two-way valve 71 mounted upon said framework.

Said valve has a two-position control element 73. In one position the rinsing fluid from pump 59 passes through one of the outlets of said valve through conduit 75 to the inlet 77 of the rinse water tank 79, FIG. 1.

Figure 4:
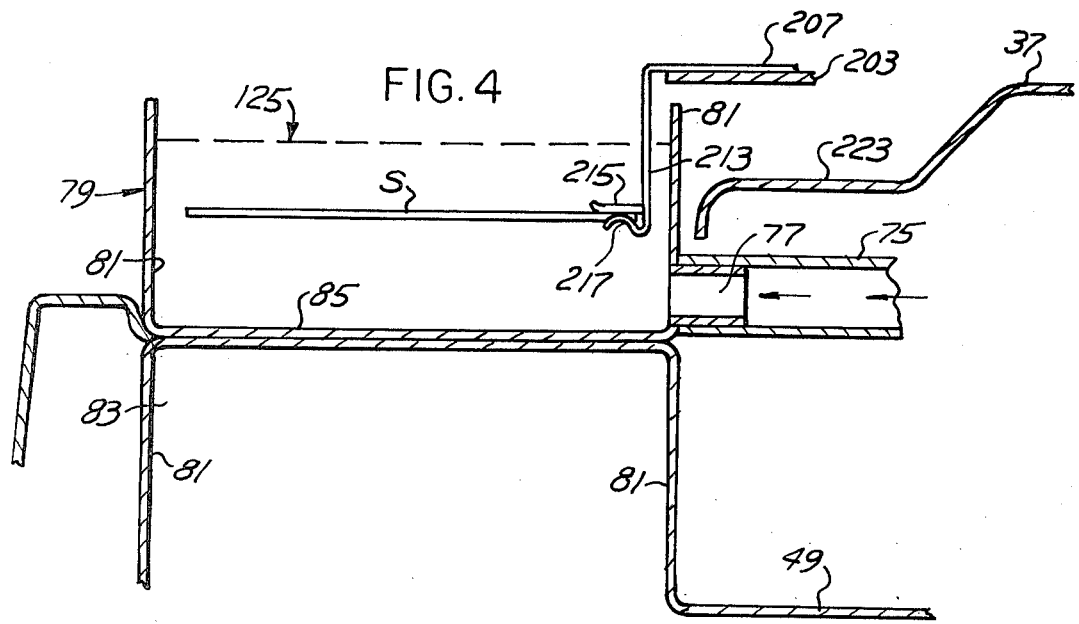
FIG. 4 is a fragmentary section taken in the direction of arrows 4—4 of FIG. 1, showing the construction of the rinse tank.

Said rinse water tank includes a pair of inner and outer arcuate walls 81 and the spaced radial side walls 83. As shown in FIGS. 4 and 5, said walls extend downwardly and are connected to the reservoir tank 49 for communication therewith.

The rinse tank 79 includes below its inlet 77 a top plate 85 which is spaced below the upper edges of the tank walls and provides a rinsing bath 125. Plate 85 at one end has an upwardly extending weir 87, FIG. 5, which is spaced from the adjacent rinse tank radial wall 83 to define an outlet passage for the overflowing liquid which descends into the reservoir tank 49.

Rinse tank 79 projects up through an aperture formed within the cover and is in registry with the annular channel 35 inwardly of the bead 31, FIGS. 1 and 2.

The weir 87 within the rinse tank maintains the proper water level in the rinse tank or dish, regardless of the quantity of water in the reservoir. Such weir can be applied to any other dish, in any procedure whose fluid level is critical.

Directly adjacent the rinse tank and nested within the annular inset platform 35 is an arcurate stain dish 91 which extends over approximately 90 degrees, for example. Said stain dish includes inner and outer concentric arcuate upright walls 93, radial end walls 95 and flat bottom 97 which nests within annular platform 35 in said cover.

The stain dish conains a solution which includes a suitable dye and other agents which are volatile and reaches an average liquid level, such as shown at 99, FIG. 2.

Upright cylindrically shaped filter 101 containing a replaceable and conventional filter element is mounted upon top platform 103 forming a part of the cover outwardly of bead 31, FIG. 1.

Said filter includes inlet 107 and outlet 109.

The conduit 105 within the framework is at one end connected to the second outlet of the valve 71 and at its other end is joined to the filter inlet 107. An additional flexible conduit 111 is connected to the filter outlet 109, extends through the framework and is connected to the rinse tank inlet 77 employing a suitable fitting which also receives the first mentioned flexible conduit 75 from valve 71.

Accordingly, in one position of the valve element 73, a rinsing liquid such as distilled water from conduit 69 and the pump passes through the valve 71 and through conduit 75, directly to the rinse tank. By manually moving the element 73 to a second position, said rinse fluid travels through conduit 105 through the filter 101 and is then directed to the rinse tank 79 by conduit 111.

As shown in FIGS. 1 and 6, a stirring motor mount bracket 113 is positioned within said framework upon base plate 13 and includes an apertured top plate 115 from which is suspended the motor 117. Its upright shaft 119 mounts at its upper end the horizontally disposed stirring bar 121 of a suitable magnetic material. Said stirring bar is arranged closely adjacent the undersurface of the platform 35 within which is nested the stain dish 91.

An elongated stirring magnet 123 rests within and upon the bottom wall 97 of the stain dish and is magnetically responsive to and rotatable in unison with stirring bar 121. Rotation of the stirring magnet causes the desired amount of agitation of the fluid within the stain dish to avoid settling therein and to keep the solution agitated for the uniform application of stain to the hemotology or other slides which pass longitudinally therethrough.

Referring to FIG. 4, illustrating fragmentarily the rinse tank 79, the fluid level is shown at 125. The water therein is turbulent due to the action of pump 59 which is constantly delivering rinse water from the reservoir tank into the rinse tank where it passes over the weir 87, FIGS. 1 and 5. The rinse tank is of sector as shown at 79, FIG. 1, as is also the stain dish 91.

The solution dish 127 also of sector form is aligned with the stain dish and nested down into the depressed platform 35 within the cover and is in lateral registry with said stain dish. Dish 127 is relatively narrow compared to the arcuate length of the stain dish and includes concentric arcuate walls 129 and the radial walls 131 and flat bottom wall 133. Said dish is adapted to contain a stain or other solution into which the hemotology or other slides are initially emersed and moved therethrough before the slides are projected through the solution within stain dish 91 for longitudinal horizontal emersion and transport therethrough.

Referring to FIGS. 1 and 3, within the framework and upon the base plate 13, there is provided fan motor bracket 135 which supports the fan motor 137 whose upright output shaft 139 centrally mounts the blower blade 141 for creating a draft causing the movement of air and any fumes from the respective dishes and tank so as to move through the arcuate inlet 47 down into the hood 41 and into the cylindrical chamber 39 depending from said cover and leading to the interior of the framework.

The framework is enclosed and reasonably sealed off by the cover side walls, front wall and rear wall. There is provided upon the diametrically opposed side of the framework a filter box 143, FIG. 2, which depends from base plate 13 and is in communication with the interior of the chamber as by the intake apertures 149.

Said filter box has a generally rectangular filter chamber within which is nested a suitable charcoal or other filter 145 for receiving the mixture of air and fumes from the respective dishes and rinse tank for delivery out from the framework through outlet 151 at the bottom of the filter box. Felt seal 147 overlies the charcoal filter, to provide an air seal and a vibration damper.

The framework for the present automatic slide stainer is adapted for support upon a suitable table as shown at 153, fragmentarily in FIG. 2. This provides adjacent outlet 151 a slide-drying area 155 upon which the unprocessed slides with freshly made blood smears may be placed. This reduces the drying time required before a smear can be stained.

Within the hollow framework of the slide stainer and upon the base plate 13 there is mounted an elongated upright bracket 157. Said bracket at its ends has a pair of spaced apart laterally extending bases 159 which are secured, as by fasteners 161, FIG. 1, to base plate 13, FIG. 1.

Intermediate the ends of said bracket there is provided the laterally extending apertured top plate 163, FIG. 2. Drive motor 165 is mounted upon bracket 157 intermediate its ends and includes the drive shaft 167 and mounted thereover the worm gear 169. Said gear is in mesh with the horizontally disposed ring gear 171 whose hub 173 is secured upon the upright preformed rotatable hub assembly 175.

The upright unit hub 175 is axially disposed through an aperture within the bracket top plate 163. The hub includes the bearing 177 whose annular flange 179 is nested within the universally adjustable bushing 181 supported between the bushing cups 183 and adjustably secured in position by the fasteners 185 to the top plate of said bracket. The hub includes the hub disc 187 adjacent its upper end whose inset annular support disc 189 projects through a corresponding aperture within the cover 37 and includes the upright center boss 191, FIGS. 1 and 2.

The circular slide retainer mount plate 193 has a central aperture to receive the center boss 191 and is secured over the top of support disc 189 by a series of fasteners 195, FIG. 2. The mounting plate 193, hereafter referred to as the slide retainer mounting plate, has a circular upwardly and outwardly tapered rim 197.

A series of slide retainers 207 are arranged around the periphery of the retainer mount plate 193 and are hingedly connected thereto throughout 360 degrees, as desired. For this purpose there is provided for each slide retainer an elongated rectangular living hinge 199 made of a suitable plastic material which has a long life and which is capable of continuous bending to define the hinge mounting for the respective slide retainers. The hinge is of polypropylene.

Each of the hinges includes an elongated rectangular strip 199 of flexible plastic material which underlies peripheral portions of plate 193 and is secured thereto by inner pop rivet 201 and the outer locating stud 202. The stud is cast into the strip and provides radial directional orientation and stabilization or any other fastening means, FIG. 2.

Flexible hinge strip 199 extends outwardly of said mounting plate 193, merging into the flexible hinge element 203 which extends along the outer surface of rim 197 to the top edge thereof and terminates in the right-angular tab 205. This tab loosely engages the edge of the rim for holding the flexible hinge element 203 in the raised secured position shown in solid lines in FIG. 2.

A series of right-angularly shaped slide retainers are mounted upon and extend radially outward of the respective flexible hinge elements 203. Each of the slide retainers includes a base 207, FIG. 2, which overlies the flexible hinge element 203 and is suitably secured thereto as by inboard stud 202 and outboard pop rivet 211. Said studs in the illustrative embodiment, are in the nature of molded projections which extend outwardly from the plastic living hinge 199 and provide with the rivets one means for mounting the hinge upon the undersurface of the slide retainer mounting plate 193 and for further securing the base portions of the slide retainers on the outer flexible hinge element 203 of said living hinge.

Each of the slide-retainer bases 207 have a central aperture to provide a clearance for receiving tab 205 projecting from the end of hinge elements 203. Tab 205 yieldably retains the slide retainer in a raised position. The slide retainers 207, 213 are preferably of stainless steel for structure and weight.

Right angular tab 267 at one end of base 207 extends through a slot 269 in hinge strip 199. Said tab engages boss 271 on the under side of strip 199 to limit hinge action to the horizontal position in FIG. 12.

Each of the slide retainers includes the right-angularly related arm 213 which mounts at one end a right-angularly positioned slide-retaining spring clip. The spring clips are of injection molded plastic having spring characteristics to receive the slides S. A preferred material is Celcon to provide a spring action that will hold the slides secured throughout the procedure, yet allow stripping the slides without binding.

As best shown in FIGS. 1 and 2, each of the spring clips include top outer clips 215 and spaced below the central lower clip 217. Each of these clips are formed to facilitate manual insertion of slide S at one end into the respective clips so as to extend radially outward therefrom. The base 216 of the spring clip underlies the outer portion of slide retainer arm 213 and is secured thereto by pop rivet 201.

A shown in FIGS. 12, 13 and 14, the slide-holder has some unique features. The webs 263 extending from the outer tabs 215 to the lower center tab 217 allow the rinse water to travel to the lower center collection point. This collection of rinse water can then be removed by passing over a water absorbent sponge material assuring the assembly of complete drying action in a limited time period. The opening 265 in the lower center portion allows air passage to further enhance the drying of both the slide and holder. This opening allows air to pass from inside the machine, through the slide-holder and back through the drying chamber.

The slide retainers 207-213 have a raised secured position such as shown in FIG. 2 with the slide retainer bearing against the rim 197 of the slide retainer mounting plate 193. Each of the slide retainers has a horizontal position as shown in dash lines at S in FIG. 2. This corresponds to the slide emersion position and is a position that the slide takes as connected to the slide retainer during normal rotary movements of the slide mounting plate 193. The slide retainers also have an intermediate dish wall clearance position, FIG. 2.

When the slide S is assembled with respect to the slide retainer 207 as in FIG. 2, the combined weight of the slide and slide retainer causes the assembly to rotate from the raised position to the horizontal emersion position.

The path of horizontal rotation of the respective slides is designated at 221, FIG. 1, and wherein the slides move continuously throughout 360 degrees in one revolution and in a predetermined time period of 15 minutes approximately. The single revolution time may be adjusted for varying stain procedures, by modifying the gearing, for example.

With the slides arranged in their emersion position extending horizontally it is necessary for the slide retainers to be momentarily elevated to the intermediate raised position in each case as the slide retainer and connected slide moves to adjacent or upright radial wall of the respective dishes 127, 91 and the corresponding rinse tank 79.

Therefore, for this purpose there is provided around the top of the cover at the correct locations a series of spaced cam means which are mounted upon the cover and are so arranged in the path of rotary movement of the corresponding slide retainer and hinge such as to, in each case as required, cam the slide retainer and its connected hinge to a raised position to permit clearance of the slide retainer over the side edge of the respective dishes and tank.

For example, there are a plurality of properly located cam rollers 225 as shown in FIG. 1 so that the respective slide retainer is cammed to raised position to clear the adjacent side wall 131 of dish 127.

As soon as the slide retainer clears that wall, upon continued movement in a circular direction, it drops by gravity so that the slide is emersed in the liquid within the said dish and moves horizontally therethrough until it reaches the other radial wall 131 of said dish. At that time, there is located an additional cam roller 225 which momentarily raises the slide retainer so that the slide clears that wall and during continuous rotation thereafter, the slide retainer and connected clip drops by gravity down into stain dish 91 for continued horizontal translation through the staining liquid therein. This is illustrated fragmentarily in FIG. 4. On continued rotation of the slide retainer mount plate 193 under the drive of the motor 165, the blood specimen or other material on the horizontally disposed emersed slide is being stained by the stain solution which is being agitated continuously by the magnetic stirrer 123, FIG. 6. As the respective slide retainer and slide reaches the far radial wall of the stain dish, there is again located, as shown in FIG. 1, a further cam roller 225 which momentarily elevates the slide retainer to its raised position so as to clear the end wall of said stain dish and to, at the same time, clear the adjacent radial wall of rinse tank 79 and the weir 187.

An additional cam roller 225 is shown, FIG. 1, adjacent the far radial wall of rinse tank 79 so that after the corresponding stained slide has been rinsed by the agitated and continuously moving rinse water within the rinse tank, there will be an automatic camming of the corresponding slide retainer to the raised position lifting the slide so as to clear said wall. Immediately thereafter and by gravity, the slide retainer tilts down to the horizontally disposed lower position. Continued rotation of the slide retainer brings the now wet, but rinsed, mounted slide into the lateral inlet 42 of the drying chamber 43 within the hood 41, FIG. 3.

Before entering the drying chamber the lowered slide holder clips 215, 217 passes over and contacts a water absorbant sponge material 273 to remove the waterdrop collected at the bottom centers of the slide holder.

Accordingly, the stained and rinsed slide is now translated slowly through the drying hood and chamber 43 and moves through a corresponding hood outlet 44 towards the slide unload container 247, FIG. 1. Again in advance of the first radial side wall 249 of this U-shaped container, there is provided an additional cam roller 225 to, again, momentarily elevate the corresponding slide retainer to its raised clearance position merely to pass over this radial wall of the unloader after which, the slide retainer pivots through its flexible hinge assembly 203 to the lower position again. As the slide retainer moves transversely of the slide unload container, eventually the stained and now reasonably dried slide will be stripped from the corresponding slide retainer clip by engagement of the slide with the far radial wall 249 of the unload container 247. Accordingly, on continued rotation of the slide support, the respective slides will accummulate in a stack within said radially directed unload container.

For each of these cam means, at the right time during rotary movement of the slide retainer and associated clipped on slide, the cams are effective for momentarily elevating the corresponding slide retainer to a clearance position and thereafter, by gravity, the assembled clip and slide retainer move by gravity to the normal horizontal position.

One of the cam means is shown in detail in FIG. 2. Spaced around the platform 223 forming a part of the cover the cam rollers 225 are upon radial journals 227 on upright brackets 229. The base 231 of each of the said brackets is adjustably secured by fasteners 233 to platform 223.

Each of the cam means 225 are of the same construction and are adjustably positioned in the correct places to effect the momentary elevation of the associated slide retainer. The cam means 225 adjacent the rinse tank is extended so that the slide holder passes over weir 87.

Figure 9:
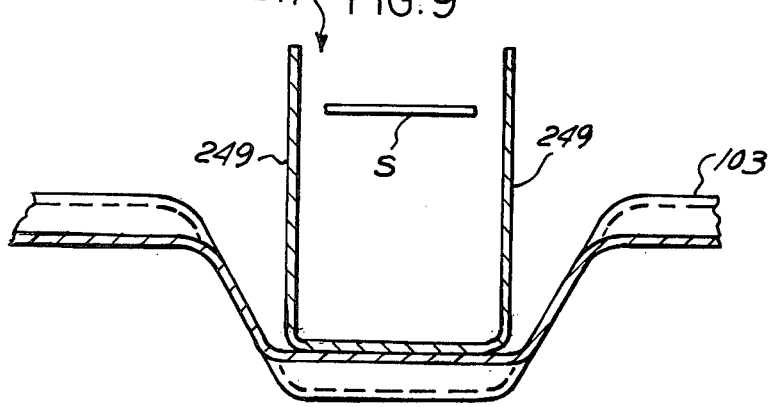
FIG. 9 is a fragmentary section taken in the direction of arrows 9—9 of FIG. 8.

With the slide retainers moving horizontally within the U-shaped unload container 247, the corresponding slide retainer is still in its lowermost position and passes through the inward downwardly extending slots 251 at the inner ends of the side walls 249 of the unload container, FIGS. 8 and 9.

Figure 10:
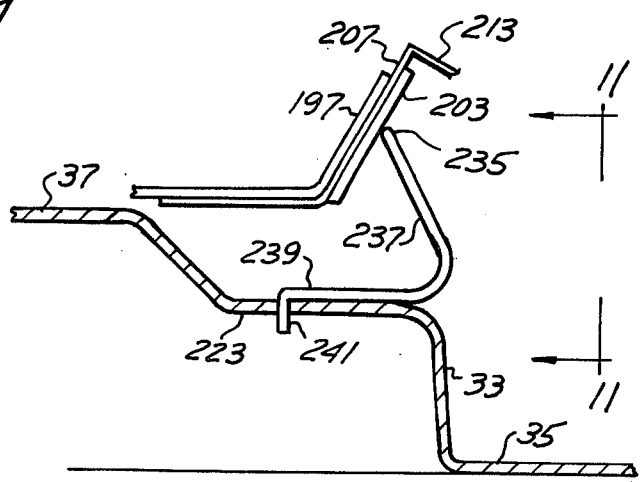
FIG. 10 is a fragmentary section taken in the direction of arrows 10—10 of FIG. 1, illustrating a wire cam device.
Figure 11:
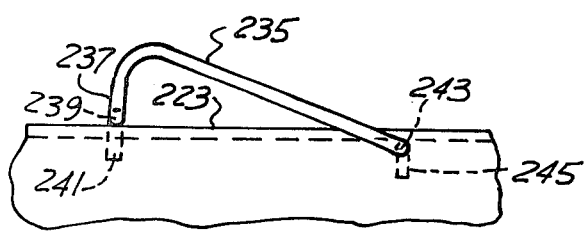
FIG. 11 is a fragmentary section taken in the direction of arrows 11—11 of FIG. 10.
Figure 7:
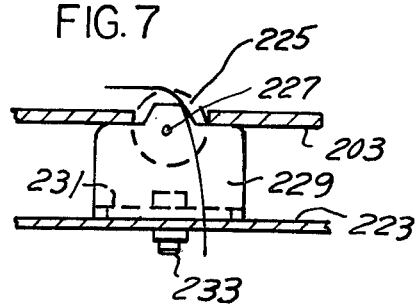
FIG. 7 is a fragmentary section taken in the direction of arrows 7—7 of FIG. 2, illustrating the slide retainer cam mechanism.

A wire cam is shown in FIG. 1 and in further detail in FIGS. 10 and 11 downstream of the unload container. As viewed in FIG. 10, the cam wire has at one end, the trailing end, the support portion 237 which has radial inturned base 239 and a right-angular anchor 241 which extends through a corresponding aperture in platform 223.

As shown in FIG. 11, the wire cam includes an upwardly inclined portion 235 whose lower end has a radially-extending base portion 243 which terminates in the downturned anchor 245. This anchor portion of the wire cam also extends through a corresponding aperture in the top platform 223 for supporting the wire anchor in the upright position shown. This is the position of the wire cam looking at it from its side. On continued rotation of the unloaded slide retainer 207, it will engage the lower portion of the wire cam 235 and on continued rotation thereof, will cause the slide retainer to be tilted to its raised secured position, FIG. 2, bearing against rim 197.

Accordingly, as each of the successive slide retainers as unloaded move from the unload container 247, they will be cammed to the raised secured position as shown in a group in FIG. 1, ready for the manual loading of additional hemotology or other slides S.

Referring to FIGS. 8 and 9, there is shown the detail of the construction of the unload container 247. Said container is of U shape, open at its top and includes a pair of laterally spaced upright parallel side walls 249. The forward edges of the side walls are slotted or cut away as at 251, FIG. 8.

Overlying the cover and enclosing from the outside of the turn table or slide retainer mount plate 193 and hood 41 is a formed hood 253 made of a suitable transparent plastic material. Said hood includes top wall 255, FIG. 2, rear wall 257, and the opposed side walls 259. The forward portion of the hood is open as shown at 261, permitting air communication to the interior thereof, and to facilitate the loading of the slides to the slide retainers.

Since the solutions employed in the solution dish 127 and within the stain dish 91 as well as to some extent within the rinse tank 79, are volatile and these fumes would be normally harmful to breath, the present hood functions to contain such fumes which are drawn by the draft created into the hood 41 by the suction blower 141. The fumes so collected move through the interior of the framework and into the filter box 143 with the fumes absorbed by the charcoal filter 145 and with fresh clean air exiting at 151 at the front of the stainer.

While the foregoing device has been referred to as a hemotology slide stainer, it is regarded as equivalent that the stainer may be used for other types of slides. For example, the material upon the slide may be tissue material, pap smears, bone marrow, etc.

Having described my invention, reference should now be had to the following claims.

I claim:

1. In an automatic slide stainer, a hollow enclosed framework including a base and a cover with front, rear and side walls;
   said cover including an outer annular platform;
   a first dish of limited width having a flat bottom mounted upon said platform, adapted to contain a chemical solution;
   a stain dish of increased width having a flat bottom mounted upon said platform at one side adjacent said first dish, adapted to contain a stain solution;
   a reservoir tank mounted upon said base within said framework, having an outlet, and adapted to contain a rinse solution;
   a rinse tank connected to and in communication with said reservoir tank, projected up through an aperture in said platform and adjacent the other side of said stain dish, and having an inlet above said reservoir tank;
   a motor-operated pump mounted upon said base within said framework, and having an inlet and outlet;
   conduits respectively interconnecting the reservoir outlet and pump inlet, and pump outlet and rinse tank inlet, for the continuous circulation of rinse liquid through said rinse tank;
   a power rotated upright hub journalled and supported upon and within said framework centrally of said platform and projecting through and above said cover;
   a drive means upon said framework connected to said hub;
   a disc shaped slide retainer plate mounted upon and centrally secured to said hub for rotation radially inward of said dishes and tank;
   a series of radially extending slide retainers pivotally mounted upon said plate around its periphery, each retainer having an outwardly directed spring clip adapted to supportably and frictionally receive one end of a slide to be stained;
   said slide retainer and clip having a raised secured position, a raised slide clearance position and a lowered horizontal slide immersion position for translation within the fluids in the respective dishes and rinse tank;
   said slide retainers, when supporting a slide, being normally biased to immersion position;
   and a series of spaced cam means mounted upon said cover inwardly of said platform, normally in the path of rotative movement of said slide retainers and slides for movably camming the retainers successively to raised slide clearance position;
   said cam means being located adjacent and in advance of the radial sides of each dish and tank so that said retainers and connected slide are temporarily cammed to raised clearance position to clear the dish and tank sides during continous rotation thereof.

2. In the slide stainer of claim 1, said annular platform being vertically offset defining an outer peripheral bead; said cover having a flat inner raised platform concentric to and spaced radially inward of said bead; said bead and platform defining an annular groove within said cover; said dishes being snugly nested within said annular groove.

3. In the slide stainer of claim 1, said dishes and tank having inner and outer circular walls and radial end walls.

4. In the slide stainer of claim 1, said reservoir tank having a drain fitting extending through said base.

5. In the slide stainer of claim 1, a horizontally disposed top plate within said rinse tank below its inlet, at one end spaced from the corresponding end wall of said rinse tank defining an elongated liquid outlet to said reservoir tank.

6. In the slide stainer of claim 5, an upright weir on said top plate spaced from a side wall at one side of said outlet over which the rinse liquid flows.

7. In the slide stainer of claim 1, a bracket on said base supporting said pump.

8. In the slide stainer of claim 1, a rinse water filter mounted upon said cover having an inlet and an outlet; a conduit interconnecting said filter outlet and rinse tank inlet; a selector valve on said framework having an inlet and first and second outlets; a conduit interconnecting the valve first outlet and said filter inlet; the conduit between said pump outlet and said rinse tank inlet having a first branch connected to the valve inlet and a second branch interconnecting the valve second outlet and said rinse tank inlet, whereby in one position of adjustment of said selector valve the pumped liquids pass through said filter before going to said rinse tank, and in another position bypass said filter.

9. In the slide stainer of claim 1, the support of said power rotated hub including an elongated upright bracket mounted upon said base within said framework and including a top apertured horizontal web below said cover; said hub being disposed through said web; and an end thrust bearing mounted upon said web adjustably supporting said hub.

10. In the slide stainer of claim 9, said bearing being universally adjustable for presetting the axis of rotation of said hub.

11. In the slide stainer of claim 9, a ring gear axially secured upon said hub; said hub drive means including a motor mounted upon said bracket having a horizontal drive shaft; and a gear on said drive shaft in mesh with said ring gear.

12. In the slide stainer of claim 11, said hub and connected slide retainer plate adapted for one complete rotation in a preset time period in the range of 5 to 15 minutes.

13. In the slide stainer of claim 1, an annular upwardly and outwardly inclined rim on said slide retainer plate; portions of said slide retainers in their raised position bearing against said rim.

14. In the slide stainer of claim 13, the pivotal mounting of each slide retainer including an elongated radially extending rectangular strip of flexible plastic material partly underlying said slide retainer plate and secured thereto; with an outer portion of said strip extending along said rim to the top thereof.

15. In the slide stainer of claim 14, portions of said slide retainers being mounted on and secured to said strip outer portion.

16. In the slide stainer of claim 14, a flexible retainer upon the outer end of the outer portion of said hinge strip loosely and frictionally engaging said rim to hold said slide retainer in a raised position when unloaded.

17. In the slide retainer of claim 14, said hinge strip having a series of rivets projecting therefrom adapted for interlocking with edge portions of said slide retainer plate and portions of said slide retainer.

18. In the slide stainer of claim 14, said slide retainer being right angular in shape with one end overlying and secured to said hinge strip, its spring clip extending at right angles to its other end.

19. In the slide stainer of claim 18, said spring clip being of a plastic material, with a portion thereof underlying the other end of said slide retainer and secured thereto.

20. In the slide stainer of claim 18, said slide retainer one end terminating in a right angular flange projecting through a central opening in said hinge strip; and stop means depending from said hinge strip engagable with said flange to limit pivotal movement of the other end of said slide retainer.

21. In the slide stainer of claim 14, a slide unload container mounted upon said cover in the path of rotary movement of said slide retainers and slides having a pair of upright radially extending spaced walls; there being an additional cam means on said cover in the path of movement of said slide retainers; for momentarily pivoting each slide retainer to its raised position to clear the adjacent one wall of said unload container, said retainer and slide automatically dropping to its horizontal position within said unload container; continued rotary horizontal movement of each slide retainer stripping its slide therefrom as it engages the other wall of said unloader container, said slides accummulating in a stack within said unload container.

22. In the slide stainer of claim 21, and additional cam means on said platform adjacent said slide unloader container downstream thereof, for operative engagement with each unloaded slide retainer camming them successively to their raised secured position.

23. In the slide stainer of claim 14, said plastic strip having upon its under surface intermediate its ends a transverse notch defining a pivot line.

24. In the slide stainer of claim 1, said cam means including a plurality of upright angle brackets adjustably mounted upon said cover; and a roller mounted upon each bracket upon a horizontal radial axis; said slide retainers on rotation being successively commed upwardly by said rollers.

25. In the slide stainer of claim 1, a stirring motor mounted upon said base within said framework and having an upright drive shaft arranged below said stain dish; a horizontally disposed stirring bar of magnetic material centrally secured to said shaft for rotation below and closely adjacent said cover; and an elongated stirring magnet within and upon the bottom of said stain dish and rotatable within the fluid therein, being magnetically responsive to rotating movements of said stirring bar for rotation in unison therewith.

26. In the slide stainer of claim 1, a slide dryer downstream of said rinse tank including a circular hood having a top wall formed in said cover and spaced above the plane thereof defining with said cover an arcuate air intake aperture; a cylindrical wall depending from said platform below said hood defining a fume exhaust chamber communicating with the interior of said framework; and a suction fan mounted upon said framework projecting up into said exhaust chamber; spaced sides of said hood being open so that said slide retainers and slides pass horizontally through said hood.

27. In the slide stainer of claim 26, an electric resistance heating element supported upon the interior of said hood.

28. In the slide stainer of claim 26, a hood with depending side and rear walls at their lower edges mounted upon and overlying said cover and defining an enclosure for retaining the fumes from said dishes and rinse tank, so that these are confined and drawn into said slide drying hood and fume exhaust chamber..

29. In the slide stainer of claim 28, the forward side of said latter hood being open for manual access to said slide retainers, for loading the same, and to permit the flow of ventilating air into said latter hood.

30. In the slide stainer of claim 28, there being an exhaust chamber upon and depending from said base, communicating with the interior of said framework; and diametrically spaced from said circular hood, said exhaust chamber outletting to atmosphere; and a filter medium within said exhaust chamber for absorbing chemical fumes before exhausting thereof.

31. In the slide stainer of claim 30, a felt strip within said exhaust chamber overlying said filter medium serving as a seal and vibration damper.

32. In the slide stainer of claim 26, a slide unloader container mounted upon said cover in the path of rotary movement of said slide retainers and slides having a pair of upright radially extending spaced walls; there being an additional cam means on said cover in the path of movement of said slide retainers; for momentarily pivoting each slide retainer to its raised position to clear the adjacent one wall of said unload container, said retainer and slide automatically dropping to its horizontal position within said unload container; continued rotary horizontal movement of each slide retainer stripping its slide therefrom as it engages the other wall of said unloader container, said slides accummulating in a stack within said unload container.

33. In the slide stainer of claim 1, a slide unload container mounted upon said platform in the path of rotary movement of said slide retainers and slides, having a pair of upright radially extending spaced walls; there being an additional cam means on said cover in the path of movement of said slide retainers, for momentarily pivoting each slide retainer to its raised position to clear the adjacent one side wall of said unload container, said retainer and slide automatically dropping to its horizontal position within said unloader; continued rotary movement of each slide retainer stripping its slide therefrom as it engages the other wall of said unload container, said slides accummulating in a stack within said unload container.

34. In the slide stainer of claim 33, and additional cam means on said platform adjacent said slide unloader container downstream thereof, for operative engagement with each unloaded slide retainer camming them successively to their raised secured position.

35. In the slide stainer of claim 34, said additional cam means including a wire having an upwardly inclined portion in the path of movement of said slide retainer, its end portions being secured to said platform.

36. In the slide stainer of claim 1, said dishes and rinse tank being sector-shaped, with the side walls of the stained dish respectively engaging the adjacent side walls of said first dish and rinse tank.

37. In the slide stainer of claim 1, an absorbant sponge on said cover downstream of said rinse tank adjacent the path of horizontal movement of a slide retainer and slide and lightly engagable therewith for collecting excessive fluid thereon.

* * * * *